United States Patent [19]

Nevin

[11] 4,273,920

[45] Jun. 16, 1981

[54] POLYMERIZATION PROCESS AND PRODUCT

[75] Inventor: Robert S. Nevin, Indianapolis, Ind.

[73] Assignee: Eli Lilly and Company, Indianapolis, Ind.

[21] Appl. No.: 75,296

[22] Filed: Sep. 12, 1979

[51] Int. Cl.$^3$ .................... C08G 63/06; C08G 63/04
[52] U.S. Cl. .................... 528/361; 528/354; 528/356; 424/19; 424/20; 424/32; 424/78; 128/335.5
[58] Field of Search ............... 528/361, 354, 355, 356, 528/357, 358

[56] References Cited

U.S. PATENT DOCUMENTS

| | | | |
|---|---|---|---|
| 2,362,511 | 11/1944 | Teeters | 528/361 |
| 2,703,316 | 3/1955 | Schneider | 260/78.3 |
| 2,758,987 | 8/1956 | Salzberg | 260/78.3 |
| 3,268,487 | 8/1966 | Klootwijk | 260/78.3 |
| 3,442,871 | 5/1969 | Schmitt et al. | 260/78.3 |
| 3,458,622 | 7/1969 | Hill | 424/19 |
| 3,535,419 | 10/1970 | Siegrist | 424/22 |
| 3,736,646 | 6/1973 | Schmitt et al. | 29/458 |
| 3,773,919 | 11/1973 | Boswell et al. | 424/19 |
| 3,839,297 | 10/1974 | Wasserman et al. | 260/78.3 R |
| 3,887,699 | 6/1975 | Yolles | 424/19 |
| 3,991,766 | 11/1976 | Schmitt et al. | 128/335.5 |
| 4,011,312 | 3/1977 | Reuter et al. | 424/78 |
| 4,144,317 | 3/1979 | Higuchi et al. | 424/21 |

OTHER PUBLICATIONS

"Slow-Release Bolus", p. 11, Oklahoma Farmer-Stockman, Feb. 1979.

*Primary Examiner*—Earl A. Nielsen
*Attorney, Agent, or Firm*—Charles W. Ashbrook; Arthur R. Whale

[57] ABSTRACT

Lactic-glycolic copolymers having molecular weights of about 6000 to about 35000 are prepared by condensation of lactic acid and glycolic acid in the presence of readily removable strong acid ion-exchange resins.

11 Claims, No Drawings

POLYMERIZATION PROCESS AND PRODUCT

BACKGROUND OF THE INVENTION

Polymers and copolymers are widely used in a variety of fields. One reason for the expansive application of polymers is due to the uniquely differing physical properties which are exhibited by various polymers. Numerous different polymers, all exhibiting varying physical properties, can be obtained from the same monomers by altering the method of preparation, the polymerization catalysts, the quantities of monomers utilized and related factors.

The prior art teaches a number of polymers and copolymers of lactic acid and glycolic acid. Schmitt et al., in U.S. Pat. Nos. 3,739,773, 3,736,646 and 3,875,937, cite and discuss a great deal of art directed to polymers and copolymers in general, as well as specific lactic acid and glycolic acid copolymers.

As pointed out by Yolles in U.S. Pat. No. 3,887,699, much interest has been focused on the possibility of incorporating drugs into polymeric materials in order to obtain a controlled and sustained release of such drug to a living system. Many problems, however, are associated with the use of polymers and copolymers for the slow release of drugs into a living system. For example, Schmitt et al., in U.S. Pat. No. 3,982,543, points out that copolymers in general have a relatively slow hydrolysis rate in the acid environment in the stomach but a much higher hydrolysis rate in the more alkaline environment of the intestine. Siegrist et al., in U.S. Pat. No. 3,535,419, disclose a sustained release drug and polymer formulation that is suitable for the administration of steroidal drugs via the rumeno-reticular portions of the stomach of ruminants. Such formulations require the use of at least one highly water insoluble wax, fat, oil, fatty acid, fatty acid ester, fatty acid amide, fatty acid alcohol or polymer. Reuter et al., in U.S. Pat. No. 4,011,312, describe a prolonged release drug dosage form for the treatment of bovine mastitis consisting of an antimicrobial agent dispersed in a matrix of a polyester of glycolic and lactic acids having a molecular weight of less than 2000.

Numerous references teach that an advantage of utilizing copolymers comprised of glycolic acid and lactic acid is the fact that the hydrolysis products are constituents in normal metobolic pathways and consequently are nontoxic and harmless when exposed to human or animal tissues. One drawback associated with the prior art copolymers, however, is the presence of polymerization catalysts such as a polyvalent metal oxide or metal halide. Upon biodegradation of the copolymer-drug matrix, a finite quantity of such toxic polymerization catalyst remains in the animal tissue and is not subject to biodegradation. Moreover, catalysts utilized to promote polymerization also cause breakdown of the polymer when contact is maintained. Therefore, polymers containing polymerization catalysts as impurities are subject to unpredictable degradation.

An object of this invention is to provide a process for polymerizing glycolic acid and lactic acid via condensation, such that copolymers having a molecular weight of about 6000 to about 35000 are obtained. A further object is to provide a polymerization process which permits the substantially total removal from the copolymer of polymerization catalysts, so that the copolymers so produced can be utilized as drug delivery systems, thereby permitting the complete biodegradation of the system with no residual toxic foreign substances remaining in animal tissues. A further object of the invention is to provide unique copolymers derived from lactic and glycolic acid which are capable of biodegradation over a predetermined period of time, thus allowing the controlled release of a drug dispersed therein at a predetermined rate over the period of time necessitated by the particular treatment being afforded. Still another object of the invention is to provide a method for polymerizing lactic acid and glycolic acid via direct condensation, thereby obviating the need to first prepare cyclic lactides and glycolides as preferred by the prior art. The invention therefore offers significant economic advantages over prior art polymerization processes.

SUMMARY OF THE INVENTION

This invention concerns a process for the polymerization of lactic acid and glycolic acid via direct condensation, and to the copolymers prepared by such process. More particularly, the invention provides a process for preparing a copolymer derived from about 60 to about 95 weight percent of lactic acid and about 40 to about 5 weight percent of glycolic acid. Said copolymer has a molecular weight of about 6000 to about 35,000, and an inherent viscosity of about 0.08 to about 0.30 when measured at a concentration of 0.50 g. of copolymer in 100 ml. of chloroform at 25° C. The process of the invention comprises reacting the appropriate quantity of lactic acid with the correspondingly appropriate quantity of glycolic acid in the presence of a strong acid ion-exchange resin at a temperature from about 100° to about 250° C. for about 3 to about 172 hours, and removing the strong acid ion-exchange resin therefrom.

Preferred copolymers prepared according to the process of this invention are derived from about 60 to about 90 percent lactic acid and about 40 to about 10 percent glycolic acid. The copolymers of the invention ideally have a viscosity of about 0.10 to about 0.25, and a molecular weight of about 15,000 to about 30,000. Especially preferred copolymers are those derived from about 70 to about 80 percent lactic acid and about 30 to about 20 percent glycolic acid with an inherent viscosity of about 0.10 to about 0.25.

According to the process of this invention, glycolic acid is condensed with lactic acid by reaction in the presence of a readily removable strong acid ion exchange resin. Preferred catalysts are those in the form of beads or similar solid compositions which facilitate removal, for example by filtration. Preferred catalysts include commercial resins of the gel type, such as Amberlite IR-118(H) and Dowex HCR-W (formerly Dowex 50W), as well as resins of the macroreticular type, such as Amberlyst 15 and Dowex MSC-1.

DETAILED DESCRIPTION OF THE INVENTION

According to the process of this invention, lactic acid is condensed with glycolic acid in such a way that a copolymer is formed which is derived from about 60 to about 95 percent by weight of lactic acid and from about 40 to about 5 percent by weight of glycolic acid. The polymerization process is carried out by condensing lactic acid and glycolic acid in the presence of a strong acid ion-exchange resin catalyst that is subject to convenient removal by standard methods such as filtration. The catalyst can be prepared by polymerizing styrene with any of a number of cross-linking agents such as divinylbenzene or the like. Such resin polymer is reacted with a strong acid such as sulfuric, phosphoric, tetrafluoroboric, paratoluenesulfonic, and related acids, so as to obtain a strong acid substituted cross-linked polystyrene. Such strong acid ion-exchange resins are commercially available in the form of beads and similar solid articles. Examples of commercially available strong acid ion-exchange resins useful in the present process include Amberlite IR-118(H), Amberlite IR-120, Amberlite IRF-66(H), Dowex HCR-W (formerly Dowex 50W), Duolite C-20, Amberlyst 15, Dowex MSC-1, Duolite C-25D, Duolite ES-26 and related strong acid ion-exchange resins. Various forms of these catalysts can be utilized, for example Dowex HCR-W2-H.

According to the present process, the strong acid ion-exchange resin is added to a mixture of lactic acid and glycolic acid. The polymerization reaction generally is carried out in the absence of reaction solvent. However, reaction solvents such as N,N-dimethylformamide, dimethylsulfoxide, and the like, can be utilized if desired. The amount of strong acid ion-exchange resin utilized in the condensation process is not critical to the process. Typically, the quantity of resin catalyst utilized will be an amount sufficient to effectively initiate and maintain the polymerization process. Such effective amounts routinely vary from about 0.1 to about 20 percent by weight relative to the total amount of glycolic acid and lactic acid in the reaction mixture.

Once the strong acid ion-exchange resin and glycolic and lactic acids are mixed, the reaction mixture is heated to a temperature from about 100° C. to about 250° C. Ideally the reaction is carried out in such a manner that water which is formed during the polymerization is conveniently removed, for instance by distillation. Water removal can be facilitated if desired by the application of a vacuum to the reaction vessel. Typically, any lactide and glycolide that is formed also is removed by such distillation. The polymerization reaction is driven to completion by the continuous heating and concomittant removal of water from the reaction mixture as it is formed. When the reaction is carried out at a temperature of about 100 to about 250° C., ideally from about 130 to about 190° C., the polymerization generally is substantially complete after about 48 to about 96 hours.

Isolation and purification of the copolymer thus formed are accomplished by routine methods. The strong acid ion-exchange resin can be substantially removed from the copolymer product by simply filtering the molten reaction mixture, for instance through a metal sieve of appropriate mesh size, for example mesh 20 to about 50. Alternatively, the reaction mixture can be cooled to room temperature and the copolymer can be dissolved in any of a number of organic solvents in which the ion-exchange resin is insoluble. Such solvents include chloroform, dichloromethane, benzene, xylene and the like. Once the copolymer is substantially dissolved in such organic solvent, normal filtration effects removal of the insoluble strong acid ion-exchange resin. Removal of the organic solvent from the filtrate, for instance by evaporation under reduced pressure, then affords the desired copolymer of the invention, substantially free of polymerization catalyst. If needed, the copolymer can be redissolved in a suitable solvent and again filtered, thereby substantially eliminating all traces of ion-exchange resin which might be present.

The copolymers comprehended by this invention and prepared according to the novel process described hereinabove are characterized by routine methods commonly utilized in the identification of polymers and copolymers. The relative composition of the copolymers is determined by proton nuclear magnetic resonance spectrometry. By determining the ratio of methylene protons attributable to glycolic acid units to methine protons attributable to lactic acid units, the relative ratio of total glycolic units to total lactic units is determined.

The inherent viscosity of the copolymers of this invention is determined by standard procedures utilizing an Ubbelohde viscometer. The copolymer to be analyzed is dissolved in chloroform at a concentration of 0.50 g./100 ml. The term inherent viscosity ($\eta$inh.) used herein is defined by the following equation:

$$\eta\text{inh.} = \frac{\ln \eta\text{rel.}}{C}$$

wherein ln, is the natural logarithm, C is concentration in grams/100 ml. of solution, and $\eta$rel. is relative viscosity as defined by the equation:

$$\eta\text{rel.} = \frac{t}{t_o}$$

wherein $t_o$ is the efflux time of pure solvent (chloroform herein) and t is the efflux time of the solution containing the copolymer.

The copolymers derived from lactic acid and glycolic acid which are provided by this invention and prepared according to the novel process described hereinabove are particularly well suited for use in the formulation of medicaments designed to provide a prolonged, controlled and uniform release of active agent to a biological system. Such formulations are especially useful in the therapeutic and prophylactic treatment of diseases occurring in animals which are not subject to daily treatment by conventional methods.

The copolymers of the invention have the unique physical properties which permit their controlled and uniform degradation into non-toxic and readily metabolized substances when placed in contact with animal tissue and body fluids. Moreover, because the copolymers are prepared by the novel process provided herein which permits the substantially complete removal of polymerization catalysts, no foreign substances of a toxic nature are available for absorption by body tissue. Furthermore, because the copolymers have the ability to undergo uniform biodegradation determined in part by the relative proportions of lactic acid and glycolic acid present, the particular period required for total biodegradation can be predetermined and adjusted as desired by varying the relative quantities of the respective constituents of the copolymer.

As contemplated herein, the copolymers provided by this invention can be utilized in the formulation of various drugs for the controlled release of such drug into a biological system. Drugs which can be incorporated into such formulations containing the copolymers of this invention include any such drug useful in the therapeutic or prophylactic treatment of a mammal, including humans and animals. The copolymers are particularly useful in the preparation of controlled release formulations for the treatment of animals raised for their meat or other food products to be consumed by humans, for example farm animals such as cattle, swine and the like.

Typical drugs which are ideally suited for the treatment of animals via a controlled release formulation utilizing a copolymer of this invention include antibiotics such as any of the well known penicillins, cephalosporins, tetracyclines, as well as specific agents such as streptomycin A and streptomycin B, aureomycin, tylosin and similar antibiotics.

Another class of drugs which are well suited to formulation with the copolymers of this invention for controlled release over a prolonged period of time are agents used to improve feed efficiency in animals such as feeder calves. Such agents currently are administered primarily as feed additives. Such method of administration suffers from the fact that the actual and effective dose of active agent is dependent upon the feeding habits of the animal, thus permitting uncontrolled overdosing and underdosing. Moreover, feeder stock which is range fed are unable to be treated by feed additives, whereas a formulation comprised of a suitable drug dispersed throughout a copolymer of this invention can be administered in the form of a bolus which is retained in the rumen, thus permitting the controlled release of an effective amount of active agent over a prolonged period of time lasting several weeks or months. Typical feed efficiency enhancing agents and growth promoters which can be formulated with the copolymers of this invention include monensin, lasalocid, apramycin, narasin, salinomycin and the like.

Another class of pharmocodynamic agents which can be formulated with the copolymers of this invention for controlled release include natural and synthetic hormones and related agents that function as fertility-control agents. Such drugs include estrogens, androgens, progestogens, corticoids, anabolic agents and the like.

The copolymers of this invention can be used to formulate an active agent for convenient oral or parenteral administration. For example, a copolymer derived from about 30 weight percent glycolic acid and about 70 weight percent lactic acid and having an inherent viscosity of about 0.13 can be dissolved in a suitable organic solvent such as dichloromethane. A sufficient quantity of an antibacterial agent such as tylosin or the like can be added to the copolymer solution, and the organic solvent can then be removed by evaporation so as to provide a uniform mixture comprised of about 30 percent active agent and about 70 percent copolymer. Such mixture can be extruded so as to form glass-type rods. The glass rods thus formed can be ground, powdered and suspended in a suitable oil such as sesame oil and injected subcutaneously to an animal such as a young calf for the effective prolonged treatment of infections caused by diseases such as pneumonia. By utilizing such formulation, the animal can receive a uniform dose of active agent, such as about 5 mg. per head per day, following a single injection. Total payout can occur within about seven days, or longer depending upon the particular copolymer and antibiotic utilized.

As noted above, the active agents can be formulated with the copolymers of the invention for convenient oral administration. For example, a feed enhancing agent such as monensin or the like can be intimately dispersed throughout a copolymer matrix. Such mixture can be molded into a bolus and adjusted so that once orally administered to a feeder calf, such formulation will lodge in the rumeno-reticular portions of the stomach, and thereby provide a gradual and controlled release of the feed utilization enhancing agent to the calf over an extended period of time. Such formulation thus permits young calves to be range fed throughout the entire range feeding season, with the net result that such animals more effectively produce more usuable meat than heretofore possible.

The use of strong acid ion-exchange resins, as hereinbefore pointed out, permits the substantially total removal (i.e. greater than ninety-five percent) of polymerization catalyst from the copolymers formed. This offers an additional advantage over the prior art since the complete removal of catalyst allows the production of copolymers having greatly enhanced stability. It is well known that catalysts which promote polymerization also promote decomposition. Accordingly, polymers prepared by standard processes utilizing non-removable catalysts such as ferric sulfate and the like are somewhat unstable and are subject to degradation upon formulation with active drugs, and additionally have a shortened shelf life once formulated. In contrast, the substantial removal of polymerization catalyst according to the process of this invention permits the production of unusually stable copolymers which are substantially resistant to degradation during formulation processing, and additionally have longer shelf lives than the polymers made by prior art methods.

In an effort to more fully describe the polymerization process and the product of this invention, the following detailed examples are provided by way of illustration.

EXAMPLE 1

To a 3-neck round bottom flask equipped with a condenser and thermometer were added 355.0 g. of lactic acid, 145.0 g. of glycolic acid and 5.0 g. of Dowex HCR-W2-H ion exchange resin. The mixture was stirred and heated to 130° C. for three hours, during which time 200 ml. of water were distilled and collected. After discarding the water thus produced, stirring and heating were continued and the pressure was gradually reduced by vacuum over three hours, after which time the temperature of the reaction mixture had increased to 150° C. at a final pressure of 5 torr. An additional 5.0 g. of Dowex HCR-W2-H catalyst was added to the reaction mixture, and the mixture then was heated to 170° C. at 5.0 torr for twenty-four hours, and then at 185° C. at 5.0 torr for an additional 48 hours. The molten reaction mixture next was filtered to remove most of the ion exchange polymerization catalyst, and the filtrate was allowed to cool to room temperature to give 300 g. of 65 percent lactic—35 percent glycolic copolymer. The copolymer was analyzed by proton nuclear magnetic resonance spectrometry and shown to be comprised of 65 percent by weight of lactic units.

The viscosity of the copolymer was determined in a Ubbelohde viscometer in which chloroform had an efflux time of 51 seconds at 25° C. The copolymer was dissolved in chloroform at a concentration of 0.50 g. per 100 ml. of solvent. Inherent viscosity of the copolymer was then determined according to the formulas:

$$\eta rel = \frac{t}{t_o} \quad \eta inh = \frac{\ln \eta rel}{C}$$

wherein:
$\eta rel$ = relative viscosity
$t_o$ = efflux time of solvent ($CHCl_3$)

t = efflux time of solution
ηinh = inherent viscosity
C = conc. in grams/100 ml.

The inherent viscosity of the copolymer thus prepared was determined to be 0.19 dl/g.

EXAMPLE 2

Following the general procedure set forth in Example 1, 710 g. of lactic acid and 290 g. of glycolic acid were condensed in the presence of a total of 40.0 g. of Amberlyst 15 ion exchange polymerization catalyst to afford 600 g. of a copolymer comprised of about 70 percent lactic units and about 30 percent glycolic units. The copolymer had the following viscosity: 0.18 dl/g.

EXAMPLE 3

Following the general procedure of Example 1, 355.0 g. of lactic acid were condensed with 145.0 g. of glycolic acid in the presence of a total of 10.0 g. of Amberlyst 15 ion exchange polymerization catalyst. After removing the catalyst by filtration of the molten reaction mixture, there was provided 300 g. of a copolymer derived from about 70 percent by weight of lactic acid and about 30 percent by weight of glycolic acid. The copolymer exhibited the following viscosity: 0.18 dl/g.

EXAMPLE 4

Following the general procedure of Example 1, 1080 g. of lactic acid were condensed with 252 g. of glycolic acid in the presence of a total of 25.0 g. of Dowex HCR-W2-H ion exchange polymerization catalyst to give, after removal of the catalyst, 750 g. of a copolymer which was shown by proton NMR to contain about 79 percent of lactic units and about 21 percent of glycolic units. The copolymer exhibited the following viscosity: 0.20 dl/g.

EXAMPLE 5

Following the procedure of Example 1, 432 g. of lactic acid were condensed with 101 g. of glycolic acid in the presence of a total of 5.0 g. of Dowex HCR-W2-H ion exchange polymerization catalyst to provide, after work-up, 300 g. of a copolymer derived from about 77 weight percent of lactic acid and about 23 weight percent of glycolic acid. The copolymer had a viscosity of 0.21 dl/g.

EXAMPLE 6

Following the procedure of Example 1, 432 g. of lactic acid were condensed with 101 g. of glycolic acid in the presence of a total of 2.5 g. of Dowex HCR-W2-H ion exchange polymerization catalyst to provide 300 g. of a copolymer comprised of about 76 percent lactic units and about 24 percent glycolic units. The copolymer had the following viscosities:
0.12 after 24 hours at 170° C.
0.20 after 24 hours at 185° C.
0.23 after 40 hours at 185° C.

EXAMPLE 7

The procedure of Example 1 was followed to condense 1080 g. of lactic acid with 120 g. of glycolic acid in the presence of a total of 25.0 g. of Dowex HCR-W2-H ion exchange polymerization catalyst. After workup, there was recovered 750 g. of a copolymer derived of about 89 weight percent of lactic acid and about 11 weight percent of glycolic acid having the following viscosity: 0.20 dl/g.

The copolymers provided by this invention additionally have been characterized by gel permeation chromatography (high pressure liquid chromatography) and subsequent determination of molecular weight. Gel permeation chromatography separates sample molecules by differences in effective molecular size in solution. Separation is accomplished as a result of the pore size distribution in the packing material. This analytical technique allows determinations of weight-average molecular weight, number average molecular weight, molecular weight distribution, and dispersity for polymeric materials.

Several such experiments have been carried out on the copolymers of this invention. Standard gel permeation chromatographic columns were used, and the support in each case was commercial μStyragel. All samples and standards were dissolved in a solution of 80 parts tetrahydrofuran and 20 parts dichloromethane. The indirect method (i.e. the "Q-Factor Method") of calibrating the gel permeation chromatographic columns was used to obtain molecular weight averages for the copolymers of the invention. Commercial polystyrene, with a Q Factor of 41.3, was used in the calibrations. The following Table presents several determinations of molecular weight by standard gel permeation chromatographic techniques as outlined above. A more detailed discussion of the technique utilized is presented by Slade in *Polymer Molecular Weights*, Marcel Deckker, Inc., 1975.

In the Table, column I presents the relative proportions of lactic units and glycolic units making up the copolymer analyzed. Column II gives the inherent viscosity of each copolymer analyzed. Column III reports the strong acid ion exchange resin utilized to prepare the copolymer being analyzed. Column IV presents the weight average angstrom size as determined from the gel permeation chromatographic retention time for the particular copolymer. Column V presents the weight average molecular weights for the various copolymers prepared by the process of this invention. The weight average molecular weights are determined by multiplying the Q-Factor for polystyrene (41.3) times the weight average angstrom size for the particular copolymer being analyzed.

As demonstrated in the Table, the preferred copolymers of this invention have a molecular weight from about 15,000 to about 35,000, and ideally from about 15,000 to about 30,000.

| Table of Weight Average Molecular Weights | | | | |
|---|---|---|---|---|
| Column I | II | III | IV | V |
| 80:20 | 0.18 | Amberlyst 15 | 412.3 | 17,027 |
| 80:20 | 0.19 | Dowex HCR-W2-H | 454.2 | 18,762 |
| 80:20 | 0.19 | Dowex HCR-W2-H | 819.3 | 33,837 |
| 90:10 | 0.20 | Dowex HCR-W2-H | 749.3 | 30,946 |
| 90:10 | 0.17 | Amberlyst 15 | 580.0 | 23,954 |
| 90:10 | 0.21 | Dowex HCR-W2-H | 841.5 | 34,754 |
| 70:30 | 0.12 | Dowex HCR-W2-H | 400.5 | 16,541 |
| 70:30 | 0.14 | Dowex HCR-W2-H | 299.8 | 12,382 |
| 70:30 | 0.15 | Dowex HCR-W2-H | 367.1 | 15,161 |
| 75:25 | 0.12 | Dowex HCR-W2-H | 349.2 | 14,422 |
| 75:25 | 0.19 | Dowex HCR-W2-H | 505.9 | 20,894 |

I claim:
1. A copolymer derived from the polymerization of about 60 to about 95 weight percent of lactic acid and about 40 to about 5 weight percent of glycolic acid, having an inherent viscosity in chloroform of about 0.08 to about 0.30 and a molecular weight of about 6000 to about 35000, said copolymer being substantially free of polymerization catalyst.

2. The copolymer of claim 1, said copolymer derived from about 60 to about 90 percent lactic acid and about 40 to about 10 percent glycolic acid, having an inherent viscosity of about 0.1 to about 0.25 and a molecular weight of about 15,000 to about 30,000.

3. The copolymer of claim 1, said copolymer derived from about 65 to about 80 percent lactic acid and about 35 to about 20 percent glycolic acid, having an inherent viscosity of about 0.10 to about 0.25 and a molecular weight of about 15000 to about 30000.

4. The copolymer of claim 1, said copolymer derived from about 70 to about 80 percent lactic acid and about 30 to about 20 percent glycolic acid, having an inherent viscosity of about 0.10 to about 0.25.

5. The copolymer of claim 1, said copolymer being derived from about 70 percent lactic acid and about 30 percent glycolic acid, having an inherent viscosity of about 0.10 to about 0.15.

6. The copolymer of claim 1, said copolymer being derived from about 80 percent lactic acid and about 20 percent glycolic acid, having an inherent viscosity of about 0.15 to about 0.25.

7. A process for preparing a copolymer derived by the polymerization of about 60 to about 95 weight percent of lactic acid and about 40 to about 5 weight percent of glycolic acid, said copolymer having a molecular weight of about 6000 to about 35000, with an inherent viscosity in chloroform of about 0.08 to about 0.30, comprising reacting lactic acid with glycolic acid in the presence of a readily removable strong acid ion-exchange resin at a temperature from about 100° to about 250° C. for about 3 to about 172 hours, and removing the strong acid ion-exchange resin therefrom.

8. The process according to claim 7 wherein from about 60 to about 90 parts of lactic acid are reacted with from about 40 to about 10 parts of glycolic acid in the presence of a strong acid ion-exchange resin.

9. The process of claim 8 wherein the strong acid ion-exchange resin is a sulfonic acid group containing resins.

10. The process of claim 7 wherein about 70 parts of lactic acid are reacted with about 30 parts of glycolic acid in the presence of a sulfonic acid group containing ion exchange resin for about 48 to about 96 hours to give a copolymer derived from about 70 weight percent lactic acid and about 30 weight percent glycolic acid, having an inherent viscosity of about 0.10 to about 0.25.

11. The process of claim 7 wherein about 80 parts of lactic acid are reacted with about 20 parts of glycolic acid in the presence of a sulfonic acid group containing ion exchange resin for about 48 to about 96 hours to give a copolymer derived from about 80 weight percent lactic acid and about 20 weight percent glycolic acid, having an inherent viscosity of about 0.10 to about 0.25.

* * * * *